United States Patent [19]

Schmolka

[11] 4,323,552

[45] Apr. 6, 1982

[54] HIGH FOAMING DENTIFRICE COMPOSITIONS

[75] Inventor: Irving R. Schmolka, Grosse Ile, Mich.

[73] Assignee: BASF Wyandotte Corporation, Wyandotte, Mich.

[21] Appl. No.: 262,315

[22] Filed: May 11, 1981

[51] Int. Cl.$^3$ .......................... A61K 7/16; A61K 7/22
[52] U.S. Cl. ......................................... 424/54; 424/49
[58] Field of Search ..................................... 424/49–58

[56] References Cited

U.S. PATENT DOCUMENTS

| | | | |
|---|---|---|---|
| 3,934,002 | 1/1976 | Haefele | 424/54 |
| 3,937,805 | 2/1976 | Harrison | 424/54 |
| 3,937,807 | 2/1976 | Haefele | 424/54 |
| 3,976,765 | 8/1976 | Nachtigal | 424/54 |
| 4,025,616 | 5/1977 | Haefele | 424/54 |
| 4,036,950 | 7/1977 | Baines et al. | 424/54 |
| 4,051,234 | 9/1977 | Gieske et al. | 424/54 |
| 4,130,636 | 12/1978 | Tomlinson | 424/49 |
| 4,198,392 | 4/1980 | Juneja | 424/54 |
| 4,206,198 | 6/1980 | Schmolka | 424/49 |
| 4,223,003 | 9/1980 | Scheller | 424/54 |

*Primary Examiner*—Shep K. Rose
*Attorney, Agent, or Firm*—H. Lawrence Jones

[57] ABSTRACT

A high foaming dentifrice composition comprising a cogeneric mixture of conjugated polyoxybutylene-polyoxyethylene nonionic surfactant and a cationic anti-decay agent.

9 Claims, No Drawings

HIGH FOAMING DENTIFRICE COMPOSITIONS

BACKGROUND OF THE INVENTION

1. Field of the Invention

The invention relates to a dentifrice comprising a cationic anti-decay agent and a cogeneric mixture of a conjugated polyoxybutylene-polyoxyethylene nonionic surfactant. The nonionic surfactant fails to inactivate the anti-microbial activity of the cationic anti-decay agent, is a better foamer than prior art nonionic surfactants and has good taste properties.

2. Description of the Prior Art

U.S. Pat. No. 2,828,345 relates to the preparation of polyoxyalkylene diols which are surface active hydroxypolyoxyethylene diethers of polyoxybutylene glycols. The molecular weight of the polyoxybutylene is disclosed as at least 1100, preferably 1200 to 2000 and the oxyethylene content is between 40 and 90 weight percent. In a list of disclosed utilities for these products, dispersing agent, emulsifying agent and textile detergent are emphasized. The use of these diols as a component for a dentifrice or high foaming agent is not suggested. U.S. Pat. No. 4,206,198 relates to a dentifrice containing a cationic anti-decay agent and a nonionic surfactant which is an ethoxylated adduct of $C_{15}$ or $C_{16}$ fatty alcohol in which ethylene oxide units account for 50 to 75 percent of the molecular weight of the adduct. There is no suggestion that, by utilizing polyoxybutylene as a substitute for the $C_{15}$ or $C_{16}$ fatty alcohol hydrophobe, higher foaming surfactants may be obtained.

Some of the problems associated with the prior art dentifrices have been reduction in the activity of the anticaries agent, low foaming of the surfactant and poor taste properties of the surfactant. The present invention is directed to the preparation of a dentifrice devoid of these problems.

SUMMARY OF THE INVENTION

The invention relates to a dentifrice comprising a nonionic surfactant and an effective amount of a cationic anti-decay agent, said nonionic surfactant being a cogeneric mixture of conjugated polyoxybutylene-polyoxyethylene compounds containing in their structure oxybutylene groups, oxyethylene groups and an organic radical derived from an organic compound containing a plurality of reactive hydrogen atoms, preferably a water soluble organic compound containing a plurality of reactive hydrogen atoms and 2 to 12 carbon atoms; the compounds being characterized in that all the oxybutylene groups are present in polyoxybutylene chains that are attached to the organic radical at the site of a reactive hydrogen atom thereby principally constituting a polyoxybutylene polymer; the oxyethylene groups being attached to the polyoxybutylene polymer in polyoxyethylene chains; the average molecular weight of the polyoxybutylene polymers in the mixture being at least 500, as determined by hydroxyl number, and the oxyethylene groups present constituting 60 to 85 percent, by weight, of the compound.

DESCRIPTION OF THE PREFERRED EMBODIMENTS

The nonionic surfactant of use in the invention is a cogeneric mixture of conjugated polyoxybutylene polyoxyethylene compounds having as a hydrophobe, a polyoxybutylene polymer of at least 500 molecular weight. The polyoxybutylene compounds are prepared by first condensing butylene oxide with an organic compound containing a plurality of reactive hydrogen atoms to prepare a polyoxybutylene polymer of at least 500 molecular weight, and subsequently condensing ethylene oxide thereto. The compounds used in this invention conform to the following generic formula:

$$Y[(C_4H_8O)_n\text{—E—H}]_x \qquad (A)$$

wherein Y is the residue of a water soluble organic compound containing therein x active hydrogen toms; n is an integer; x is an integer greater than 1; the values of n and x are such that the molecular weight of the compound, exclusive of E, is at least 500, as determined by hydroxyl number; E is a polyoxyalkylene chain wherein the oxygen/carbon atom ratio is at least 0.5, and E constitutes 60 percent by weight to 85 percent by weight of the compound.

The polyoxybutylene polymer, which is an intermediate in the preparation of the compounds of use in this invention, has the following structure:

$$Y[(C_4H_8O)_nH]_x \qquad (B)$$

wherein Y, n and x are defined as in Formula A above.

The preferred compounds of use in this invention are prepared by condensing ethylene oxide in an amount between 60 and 85 percent by weight of the resultant compound, with the polyoxybutylene polymer. These compounds have the following formula $$Y[(C_4H_8O)_n(C_2H_4O)_mH]_x \qquad (C)$$

wherein Y, n and x are defined as in Formula A and m has a value such that the oxyethylene groups constitute 60 to 85 percent by weight of the compound.

When ethylene oxide is condensed with a polyoxybutylene glycol of at least 500 molecular weight and derived from a butane diol initiator, the resulting compounds have the following structure:

$$HO(C_2H_4O)_{m'}(C_4H_8O)_n(C_2H_4O)_mH \qquad (D)$$

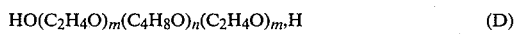

where n is defined as previously set forth; and $m'+m$ have a value such that the oxyethylene groups constitute 60 percent by weight to 85 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio obtained therein is at least 0.5.

Examples of a water-soluble organic compound containing therein x active hydrogen atoms, the residue of which is Y, are the initiators. These may include water, diols such as propane diol, butane diol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butane diol. More preferably used is 1,4-butanediol.

The butylene oxide such as 1,2-, 2,3-, 1,3- and 1,4-butylene oxide and isobutylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the surfactants used in this invention.

The preferred surfactants, conforming to structure D above of use in this invention, are those surfactants which contain a hydrophobe of about 1200 molecular weight and between 60 percent by weight and 85 percent by weight ethylene oxide; a hydrophobe of about 1800 molecular weight and between 65 percent by weight and 75 percent by weight ethylene oxide; and a hydrophobe of about 600 molecular weight and between 65 percent by weight and 85 percent by weight ethylene oxide. More preferably used is a surfactant derived from a hydrophobe of about 1200 molecular weight and containing about 70 percent by weight ethylene oxide. The surfactant is used in an amount between 0.05 percent by weight to 5 percent by weight, preferably 0.5 percent by weight to 3 percent by weight, of the dentifrice.

The cationic anti-decay agents of use in the invention may be any well known anti-bacterial agent such as the following: $N^1$-(4-chlorobenzyl)-$N^5$-(2,4-dichlorobenzyl)biguanide, p-chlorophenyl biguanide, 4-chlorobenzhydryl biguanide, 4-chlorobenzhydrylguanylurea, $N^3$-lauroxypropyl-$N^5$-p-chlorobenzylbiguanide, 1,6-di-(p-chlorophenylbiguanido)hexane, 1-(lauryldimethylammonium)-8-(p-chlorobenzyldimethylammonium)-octane dichloride, 5,6-dichloro-2-guanidinobenzimidazole, $N^1$-p-chlorophenyl-$N^5$-laurylbiguanide, 5-amino-1,3,bis(2-ethylhexyl)-5-methylhexahydropyramidine, chlorhexidine gluconate and their non-toxic acid addition salts. The cationic anti-decay agent is used in an amount between 0.01 percent by weight and 5 percent by weight and preferably between 0.05 percent by weight and 1 percent by weight of the dentifrice.

The dentifrice of the invention may be in the form of a paste, tooth powder and chewable dental tablet.

For chewable dental tablets the solids and liquids are blended similarly to toothpaste, surfactant added and a waxy matrix, such as a polyethylene glycol having a molecular weight of about 6000, is generally added in an amount between about 4 percent by weight and 20 percent by weight to facilitate tabletting.

In the preparation of tooth powders, it is usually sufficient to admix mechanically such as by milling the various solid ingredients, in appropriate quantities and partical size.

For the preparation of toothpastes, various liquids and solids are proportioned to form a creamy mass of desired consistency. Useful liquids include water, glycerin, aqueous solutions of sorbitol and propylene glycol. Preferably used is a mixture of water and a humectant or binder such as glycerine or sorbitol or both. The total liquid content is generally between 20 percent by weight and 75 percent by weight of the dentifrice. Gelling agents such as methyl cellulose, carboxymethyl cellulose and gum tragacanth are also useful. The solid portion of the vehicle is usually present in an amount of up to about 10 percent by weight, preferably 0.2 percent by weight to 5 percent by weight, of the dentifrice.

The toothpaste formulations also generally include a dentally acceptable, substantially water insoluble, polishing agent such as calcium carbonate or calcium phosphate dihydrate for dental creams or colloidal silica for visually clear gels. The polishing agent content is between 15 percent by weight and 75 percent by weight of the dentifrice for a dental cream and between 5 percent by weight and 50 percent by weight of the dentifrice for a visually clear gel.

The dentifrice may also contain a fluorine-containing compound having a beneficial effect on the care and hygiene of the oral cavity, such as sodium fluoride, or stannous fluoride, in an amount up to 1 percent, preferably between 0.1 percent by weight and 1 percent by weight of the dentifrice based on the water soluble fluorine content thereof.

Other optional additives include color whitening agents, preservatives, solubilizing agents, silicones, chlorophyll compounds, urea and diammonium phosphate. Also useful are flavoring agents such as oils of spearmint, peppermint, wintergreen, sassafras, clove, sage, eucalyptus, marjoram, cinnamon, lemon, orange and sodium methylsalicylate, sweetening agents such as sucrose, lactose, maltose, sorbitol, sodium cyclamate, perillartin saccharin and sodium saccharin. These additives are used in an amount between 0.01 percent by weight and 5 percent by weight or more of the dentifrice.

The following examples will further illustrate the various aspects of the invention. Where not otherwise specified throughout this specification and claims, temperatures are in degrees centigrade, and parts, percentages and proportions are by weight.

The following surfactants A-E, made from a polyoxybutylene hydrophobe prepared from condensing 1,2-butylene oxide with a 1,4-butanediol initiator, and comparisons M-R are used in the Examples:

Surfactant A is polyoxybutylene polyoxyethylene nonionic surfactant of this invention having an approximate average moecular weight of the polyoxybutylene hydrophobe of about 1200 and a polyoxyethylene hydrophile content of about 70 percent by weight of the surfactant.

Surfactant B is a polyoxybutylene-polyoxyethylene nonionic surfactant of this invention having an approximate average molecular weight of the polyoxybutylene hydrophobe of about 1200 and a polyoxyethylene hydrophile content of about 80 percent by weight of the surfactant.

Surfactant C is a polyoxybutylene polyoxyethylene nonionic surfactant of this invention having an approximate average molecular weight of the polyoxybutylene hydrophobe of about 1200 and a polyoxyethylene hydrophile content of about 60 percent by weight of the surfactant.

Surfactant D is a polyoxybutylene polyoxyethylene nonionic surfactant of this invention having an approximate average molecular weight of the polyoxybutylene hydrophobe content of about 600 and a polyoxyethylene hydrophile content of about 80 percent by weight of the surfactant.

Surfactant E is a polyoxybutylene polyoxyethylene nonionic surfactant of this invention having an approximate average molecular weight of the polyoxybutylene hydrophobe of about 1800 and a polyoxyethylene hydrophile content of about 70 percent by weight of the surfactant.

Surfactant M is a polyoxypropylene polyoxyethylene nonionic surfactant having a molecular weight of the polyoxypropylene hydrophobe of about 2250 and a polyoxyethylene hydrophile content of about 70 percent by weight of the surfactant.

Surfactant N is a fatty alcohol alkoxylate nonionic surfactant having a hydrophobe chain length of $C_{16}$ to $C_{18}$ and a polyoxyethylene content of about 80 percent by weight of the surfactant.

Surfactant O is a fatty alcohol alkoxylate nonionic surfactant having a hydrophobe chain length of $C_{10}$ to $C_{12}$ and a polyoxyalkylene content of about 70 percent by weight of the surfactant.

Surfactant P is a fatty alcohol alkoxylate nonionic surfactant having a hydrophobe chain length of $C_{12}$ to $C_{18}$ and a polyoxyethylene content of about 70 percent by weight of the surfactant.

Surfactant Q is a fatty alcohol alkoxylate nonionic surfactant having a hydrophobic chain length of $C_{12}$ to $C_{18}$ and a polyoxyethylene content of about 60 percent by weight of the surfactant.

Surfactant R is nonyl phenol plus 9 ethylene oxide.

EXAMPLES 1 AND 2

The following high foaming dentifrice compositions were prepared:

| Example | Parts By Weight | |
|---|---|---|
| | 1 | 2 |
| Glycerine | 30 | 30 |
| Carboxymethylcellulose | 1.7 | 1.7 |
| Sodium Saccharine | 0.2 | 0.2 |
| Water | 17.0 | 17.0 |
| Nonionic Surfactant A | 1.5 | |
| Nonionic Surfactant B | | 1.5 |
| $CaCO_3$ | 47.8 | 47.8 |
| Peppermint oil | 0.8 | 0.8 |

The above products had the consistency of toothpaste.

To the above examples 1 and 2 are aded 0.5 part sodium benzoate and 0.5 part 4-chlorobenzhydryl biguanide.

EXAMPLES 3 AND 4

The following high foaming dentifrice is prepared:

| Example | Parts By weight | |
|---|---|---|
| | 3 | 4 |
| Ethanol | 3.0 | 3.0 |
| Nonionic Surfactant A | 2.0 | |
| Nonionic Surfactant B | | 2.0 |
| Water | 24.0 | 24.0 |
| Sorbitol | 11.5 | 11.5 |
| Glycerine | 12.0 | 12.0 |
| Polishing agent $Ca_3(PO_4)_2$—$2H_2O$ | 43.5 | 43.5 |
| Silica | 1.5 | 1.5 |
| Carboxymethyl cellulose | 0.5 | 0.5 |
| Sweetener | 0.5 | 0.5 |
| Preservative | 0.5 | 0.5 |
| Peppermint oil | 0.3 | 0.3 |
| Anise Oil | 0.2 | 0.2 |
| 1,6 di (4-chlorophenyl biguanido)hexane gluconate | 0.5 | 0.5 |

EXAMPLES 5-9 AND COMPARISON EXAMPLES M-R

In order to show the superior foaming of the surfactants of use in the invention, foam tests were carried out in a dynamic foam machine as described in *Soap and Chemical Specialties,* April, 1961, "Detergent Foam Measurement", Henry E. Reich, John T. Patton, Jr. and C. V. Francis, on several of the surfactants of the invention and several comparison surfactants M-Q, at a temperature of 120° F., all at a concentration of 0.1 percent by weight of aqueous solution.

The foam heights show that the surfactants of the invention are higher foaming than the closest prior art foaming surfactants.

| Surfactant | Foam Height in millimeters at 120° F. | |
|---|---|---|
| | 200 ml/min | 100 ml/min |
| Ex 5 = A | >600 | 250 |
| Ex 6 = E | >600 | 120 |
| Ex 7 = D | >600 | 100 |
| Ex 8 = B | >600 | 210 |
| Ex 9 = C | 430 | — |
| Comp. Ex. M | 450 | — |
| Comp. Ex. N | 420 | — |
| Comp. Ex. O | >600 | 100 |
| Comp. Ex. P | >600 | 220 |
| Comp. Ex. Q | 425 | — |
| Comp. Ex. R | >600 | 210 |

The various polyoxybutylene polyoxyethylene block polymers of the invention have been found, by taste tests, to have a pleasant bland taste or were tasteless. Although P and R have foaming properties comparable to the foaming property of some of the surfactants of the invention, they have a bitter taste and destroy the antimicrobial activity of the anti-decay agent.

EXAMPLE 10

In order to demonstrate that the surfactant of the invention is compatible with the anti-decay agent, i.e. does not reduce the antimicrobial activity, the following test was conducted.

A solution comprising by weight 20 parts of a 20 percent w/v aqueous solution of chlorhexidine gluconate, 20 parts of a nonionic surfactant B (100 percent active) and 60 parts of sterile water was prepared by stirring the above ingredients in a suitable container until everything is dissolved.

The solution was diluted to a ratio by weight of 1:1024 with water and tested against *staphylococcus aureus* and *Escherichia coli* by the following test.

Soak 30 one-half inch diameter disks of very pure highly absorbent paper with the above-described diluted solution.

Prepare 5 replicate plates for each organism (i.e., 2×5 or total of 10 plates). Separately innoculate two flasks containing 150 milliliters of sterile liquid Tryptone Glucose Extract Agar (Difco 0479-01) (at temperature equal to or less than 40° C.), with 1 milliliter of 24-hour nutrient broth culture of *S. aureus* and *E. coli* respectively. Vigorously swirl contents of each flask to insure complete mixing. Add 10 milliliter portions of innoculated agar to each of the five 100-milliliter sterile petri dishes for each organism, distribute evenly and let cool and harden. As soon as the plates harden, implant three of the paper disks soaked with cleaning solution on the center of each test agar plate surface. Using blunt forceps, press each disk onto the agar surface to insure complete and uniform contact. Incubate test plates 48 hours at 37° C. Followng incubation, examine test plates to determine presence or absence of zones of inhibition around the circumference of each of the test disks.

A detectable zone of inhibition of 0.1 millimeters or greater was obtained, demonstrating that there was no significant reduction of antimicrobial activity of the chlorhexidine gluconate by the nonionic surfactant with respect to these common micro-organisms.

The embodiments of the invention in which an exclusive privilege or property is claimed are defined as follows:

1. A dentifrice comprising a nonionic surfactant and an effective amount of a cationic anti-decay agent, said nonionic surfactant being a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 500, as determined by hydroxyl number, and the oxyethylene groups present constituting 60 to 85 percent, by weight, of the mixture.

2. The dentifrice of claim 1 wherein the nonionic surfactant is a polyoxybutylene polyoxyethylene block polymer of the formula:

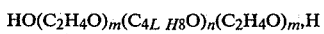

wherein m, n and m' are integers such that the polyoxybutylene chain has a molecular weight between 500 and 2000 and the polyoxyethylene chain is between 60 percent by weight and 85 percent by weight, based on the weight of the polymer.

3. The dentifrice of claims 2 wherein the surfactant is a polyoxybutylene-polyoxyethylene block copolymer of said formula having a polyoxybutylene hydrophobe molecular weight of about 1200 and a polyoxyethylene hydrophile weight percent of about 70.

4. The dentifrice of claim 2 wherein the cationic anti-decay agent is chlorhexidine gluconate.

5. A dentifrice toothpaste comprising 20 percent by weight to 75 percent by weight liquid, 75 percent by weight to 15 percent by weight polishing agent, 0.2 percent by weight to 5 percent by weight gelling agent, 0 percent by weight to 1 percent by weight fluorine containing compound, 0.1 percent by weight to 3 percent by weight additives, 0.05 percent by weight to 1 percent by weight cationic anti-decay agent and 0.5 percent by weight to 3 percent by weight polyoxybutylene polyoxyethylene block polymer of the formula:

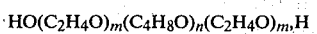

wherein m, n and m' are integers such that the polyoxybutylene chain has a molecular weight between 500 and 2000 and the polyoxyethylene chain is between 60 percent by weight and 85 percent by weight, based on the weight of polymer.

6. The toothpaste of claim 5 wherein the surfactant is a polyoxybutylene-polyoxyethylene block copolymer of said formula having a polyoxybutylene hydrophobe molecular weight of about 1200 and a polyoxyethyene hydrophile weight percent of about 70.

7. The toothpaste of claim 5 wherein the cationic anti-decay agent is chlorhexidine gluconate.

8. A tooth powder comprising polishing agent, 0 percent by weight to 1 percent by weight fluorine-containing compound, 0.1 percent by weight to 3 percent by weight additives, 0.05 percent by weight to 1 percent by weight cationic anti-decay agent and 0.5 percent by weight to 3 percent by weight polyoxybutylene polyoxyethylene block polymer of the formula:

wherein m, n and m' are integers such that the polyoxybutylene chain has a molecular weight between 500 and 2000 and the polyoxyethylene chain is between 60 percent by weight and 85 percent by weight, based on the weight of polymer.

9. A chewable dental tablet comprising 4 percent by weight to 20 percent by weight of a waxy matrix, 15 percent by weight to 75 percent by weight of a polishing agent, 0.05 percent by weight to 1 percent by weight cationic anti-decay agent and 0.05 percent by weight to 5 percent by weight polyoxybutylene polyoxyethylene block polymer of the formula:

wherein m, n and m' are integers such that the polyoxybutylene chain has a molecular weight between 500 and 2000 and the polyoxyethylene chain is between 60 percent by weight and 85 percent by weight, based on the weight of polymer.

* * * * *

UNITED STATES PATENT AND TRADEMARK OFFICE
CERTIFICATE OF CORRECTION

PATENT NO. : 4,323,552
DATED : April 6, 1982
INVENTOR(S) : Irving R. Schmolka

It is certified that error appears in the above—identified patent and that said Letters Patent is hereby corrected as shown below:

Formula in claim 2 to read as follows:

$$HO(C_2H_4O)_m(C_4H_8O)_n(C_2H_4O)_m \cdot H$$

Signed and Sealed this

Sixth Day of July 1982

[SEAL]

Attest:

Attesting Officer

GERALD J. MOSSINGHOFF

Commissioner of Patents and Trademarks